US006586653B2

(12) United States Patent
Graeme, III et al.

(10) Patent No.: US 6,586,653 B2
(45) Date of Patent: Jul. 1, 2003

(54) DISCRETE ABSORBENT ARTICLE

(75) Inventors: Robert J.. Graeme, III, Morrisville, PA (US); H. Michael Moscherosch, Doylestown, PA (US)

(73) Assignee: McNeil-PPC, Inc., Skillman, NJ (US)

( * ) Notice: Subject to any disclaimer, the term of this patent is extended or adjusted under 35 U.S.C. 154(b) by 168 days.

(21) Appl. No.: 09/825,121

(22) Filed: Apr. 3, 2001

(65) Prior Publication Data

US 2002/0143312 A1 Oct. 3, 2002

(51) Int. Cl.[7] .................................................. A61F 13/15
(52) U.S. Cl. .................... 604/375; 604/358; 604/385.01
(58) Field of Search ............................ 604/385.01, 375, 604/358, 393; 106/163.01; 162/1; 536/30

(56) References Cited

U.S. PATENT DOCUMENTS

| | | | |
|---|---|---|---|
| 3,554,788 A | | 1/1971 | Fechillas |
| 4,166,464 A | | 9/1979 | Korpman |
| 4,463,045 A | | 7/1984 | Ahr et al. |
| 4,546,029 A | * | 10/1985 | Cancio et al. ............... 428/141 |
| 4,589,876 A | | 5/1986 | Van Tilburg |
| 4,608,047 A | | 8/1986 | Mattingly |
| 4,623,340 A | * | 11/1986 | Luceri ......................... 604/370 |
| 4,687,478 A | | 8/1987 | Van Tilburg |
| 4,801,494 A | | 1/1989 | Datta et al. |
| 4,900,320 A | | 2/1990 | McCoy |
| 5,128,193 A | * | 7/1992 | Anapol et al. ............... 156/209 |
| 5,261,899 A | | 11/1993 | Visscher et al. |
| 5,458,590 A | * | 10/1995 | Schleinz et al. ............. 101/483 |
| 5,503,076 A | | 4/1996 | Yeo |
| 5,536,555 A | * | 7/1996 | Zelazoski et al. ........... 128/849 |
| 5,545,157 A | | 8/1996 | Van Iten |
| 5,562,647 A | | 10/1996 | Oetjen |
| 5,624,667 A | | 4/1997 | Maruo et al. |
| 5,763,333 A | * | 6/1998 | Suzuki et al. ................ 156/334 |
| 5,897,541 A | * | 4/1999 | Uitenbroek et al. ......... 604/358 |
| 5,961,505 A | * | 10/1999 | Coe et al. .................... 604/358 |
| D439,057 S | | 3/2001 | Bissah et al. |

FOREIGN PATENT DOCUMENTS

| | | |
|---|---|---|
| DE | 29703181 U1 | 6/1997 |
| DE | 29704994 U1 | 6/1997 |
| DE | M 9806000 | 12/1998 |
| DE | 49901952 | 9/1999 |
| DE | 2894115 U1 | 7/2000 |
| DE | 40004617 | 8/2000 |
| DE | 40007047 | 11/2000 |
| DE | 40007048 | 11/2000 |
| DE | 40005624 | 1/2001 |
| EP | 0658351 B1 | 9/1998 |
| WO | 93/09744 A1 | 5/1993 |

OTHER PUBLICATIONS

Washable Menstrual Pad With Belt at the Museum of Menstruation and Women's Health; Modern Washable Pad and Belt; 1998; Harry Finley.

Carefree panty pads for teenagers at theMuseuim of Mentruation and Women's Health; 1998; Harry Finley.

From the Collection of MUM: Snap Washable Menstrual Pad; Washable Menstrual pad, Snap–On Style; 1998; Harry Finley.

* cited by examiner

Primary Examiner—Rodney M. Lindsey
Assistant Examiner—Angela J. Grayson (57) ABSTRACT

An absorbent article having a pigmented cover; a pigmented apertured transfer layer; an absorbent core; and a pigmented backsheet that provides masking of synthetic menstrual fluid and discretion.

6 Claims, 4 Drawing Sheets

(4 of 4 Drawing Sheet(s) Filed in Color)

DISCRETE ABSORBENT ARTICLE

FIELD OF THE INVENTION

The present invention relates to absorbent articles such as pantiliners, sanitary napkins, incontinence pads, interlabial and the like. More particularly, the present invention relates to discrete pantiliners having masking properties.

BACKGROUND OF THE INVENTION

Currently, absorbent articles for sanitary protection include pantiliners, sanitary napkins, interlabial devices, and incontinence pads. These absorbent articles must fit a variety of individual body shapes and sizes and must also fit the different types of underwear available. Additionally, the options of underwear type are increasing. Not only are the shapes of the crotch changing (e.g., full-sized or conventional vs. abbreviated) but the materials and color used to make the underwear are giving woman many more choices than in previous history.

Fashion also dictates the type of underwear chosen. Pant styles, especially among the younger generation of menstruating women, can be extremely fitted. Skirts may also be short and fitted. For this reason, sanitary protection articles need to be necessarily discrete. Absorbent articles that have previously been bulky are being made thinner with the use of additives, such as super absorbent polymers, which absorb large quantities of fluid with less bulk than a conventional pulp absorbent.

Likewise, pant and undergarments are becoming more sheer making the color of absorbent articles to become increasingly more important. For example, a woman wearing a short skirt with dark, sheer pantyhose and/or a pair of dark, sheer underwear may prefer to have a corresponding colored absorbent article for sanitary protection as opposed to the traditional white.

Additionally, while increasing the overall absorptive capacity has proved to be beneficial in preventing soiling undergarments, the impression to the user, however, is that the absorbent core has reached its capacity and is near failure due to the visual presence of such fluids on the absorbent article.

Finally, there is the psychological benefit of wearing an "unsoiled" absorbent article if the user has the perception that the article is clean and dry.

These problems are partially addressed in U.S. Pat. No. 5,562,647 to Oetjen. In this patent, there is disclosed a sanitary napkin having a fluid pervious masking member disposed about the periphery of the napkin.

Additionally, U.S. Pat. No. 4,801,494 to Datta discloses masking properties that are provided by a spunbonded liner fabric material having a heavy loading of pigment in fibers of a heavier denier than generally formed into a spunbonded fabric. In particular, the fibers and filaments were disclosed as being formed of polypropylene, copolymers of polypropylene and polyethylene, linear low-density polyethylene, other polyolefins and polyesters. The larger filaments were disclosed as being easier to extrude and the lightweight of the web lowers cost as less polymer is used. Datta disclosed that the cover is formed with a large open area. This large open area was presumed to allow passing of small clots in menstrual fluid for presenting a cleaner surface. Further, Datta also postulated that by having a large open area, liquids supplied to the cover are absorbed faster, and the cover both feels and looks drier and cleaner.

Datta disclosed that the pigment or colorant could be light pink, peach and other pastel colors. In particular, a preferred color was white, which was disclosed as being formed by titanium dioxide being present in an amount between about 1 and about 6% by weight. The pastel colors were disclosed as optionally being preferred in some instances to mask certain absorbed materials with a resulting pleasing color.

Recently, Procter & Gamble (Cincinnati, Ohio) launched a black pantiliner under its ALLDAYS brand. This product has a black transfer layer and a black apertured film layer that are disposed on an absorbent core. Additionally, two black nonwoven fabric strips, that are oriented in longitudinally opposed parallel relationship about a longitudinal central zone of the black apertured film layer are provided. The general structure of this ALLDAYS product is disclosed in WO 93/097744, published May 27, 1993, to Procter & Gamble Company. While this ALLDAYS product appears black, the white absorbent core is discernible to the naked eye in the central zone of the black apertured film layer. In addition, this product suffers from poor fluid masking.

Accordingly, there is a need for an absorbent product that offers not only superior fluid masking, but does not also reveal the white absorbent core to the user. By providing such an absorbent product the user has the perception of a clean and dry product.

SUMMARY OF THE INVENTION

An absorbent article having a pigmented cover; a pigmented apertured transfer layer; an absorbent core; and a pigmented backsheet that provides masking of synthetic menstrual fluid and discretion.

DETAILED DESCRIPTION OF THE INVENTION

As used herein, masking means the property of the body facing side of an absorbent article to not visually change color upon the addition of body exudates thereon; e.g., the color of the product after having synthetic menstrual test fluid applied to the body-facing surface of the absorbent product is not visibly altered. As also used herein, pigment means inert particles that are incorporated in a material, e.g., carbon black and titanium dioxide. Naked eye as used herein means about 20/20 vision, whether corrected or uncorrected.

As used herein, all ranges provided are intended to expressly include at least all numbers that fall between the endpoints of ranges.

As is well known to those skilled in the art, absorbent articles that are worn externally generally have a layered construction with a body-facing surface that is oriented to face the wearer during use and a garment-facing surface oriented in the opposite direction from the body-facing surface. Typically such articles have a liquid pervious cover on the body-facing surface of the article, an absorbent core and a backsheet on the garmnent-facing surface of the article. The absorbent core is interposed between the cover and the backsheet. The cover and the backsheet encase all components of the article. The cover and the backsheet are typically joined or sealed to each other along their peripheral edge using any method known in the art.

Additionally, absorbent articles often include a transfer layer, which is positioned between the cover and absorbent core. The transfer layer may be any material that draws or transports fluid away from the cover and body towards the absorbent core or layer.

Commonly, materials used to make absorbent articles are white or near white.

In a preferred embodiment of the present invention, the absorbent article has a cover, a transfer layer, an absorbent core and a backsheet. A pigment, such as carbon black, is incorporated into the cover, transfer layer and backsheet, thereby providing masking of the absorbent core and discreteness of the absorbent article.

Cover

The cover of an absorbent article typically overlays the absorbent core. The exterior of the cover forms the body-facing surface of the absorbent article. As known by those skilled in the art, the cover may be formed from any fluid pervious material that is comfortable against the skin and permits fluid to penetrate to the absorbent core, which retains the fluid. The cover should retain little or no fluid to provide a relatively dry surface next to the skin when in use. A variety of cover materials are known in the art, and any of these may be used. For instance, the cover has been made from fibrous non-woven fabrics made of fibers or filaments of polymers, such as polyethylene, polypropylene, polyester, or cellulose, and combinations or mixtures thereof. The fiber or filament can be single denier or multidenier.

Other materials used in making covers include gauze or for example, a nonwoven material such as the ones described in U.S. Pat. No. 3,554,788 (Fechillas), any known porous material with a suitable body contacting surface, including, but not limited to nonwoven webs, apertured films, plastic nets, and the like. Previously, the cover could also be made from a fibrous nonwoven composite of bicomponent fibers and pulp fluff.

Alternatively, the cover may be formed from an apertured polymeric film. In addition, such a film may be treated with a surfactant to increase hydrophillicity.

Generally, the cover is a single sheet or layer of material having a width sufficient to form the body-facing surface of the absorbent article. Preferably, the cover is longer and wider than the absorbent core.

In a preferred embodiment, the cover is a web made from a spunbonded mixture of single denier polypropylene filaments containing carbon black. A preferred range of polypropylene filaments is about 95 to about 99% by weight of the web, more preferably 97 to 98% by weight of the web. Additionally, it is preferred that the material used to form the cover be hydrophilic, which can be by any methods known to those skilled in the art such as surface treatment, surface spraying or incorporation of a surfactant into the mixture. An example of such a web or nonwoven is number 7070-001H available from the Polymer Group Inc, (Benson, N.C.).

Preferred colorants include inert or inactive pigments, such as carbon black iron oxides (red, yellow, and brown), chromium oxide (green), ferric ammonium ferrocyanide (blue) and the like. Major organic pigments include diarylide yellow AAOA (Pigment Yellow 12), diarylide yellow AAOT (Pigment Yellow 14), phthalocyanine blue (Pigment Blue 15), lithol red (Pigment Red 49:1), and (Red Lake C Pigment Red. The amount of pigment used is dependent upon the individual pigment loading level. In the present invention, carbon black from Degussa (Dusseldorf, Germany) under the trade name Printex F Alpha is used, preferably at about 0.5 to about 2.8% by weight of the web, more preferably about 0.7 to about 2.0% by weight of the web. Other carbon black pigments include any FDA-approved pigment, including Printex F80, Printex F85, and Printex FP, all from Degussa (Dusseldorf, Germany) and PPM 9294 from Techmer PM (Rancho Deminguez, Calif.). Preferably, the resulting black color provides a measurement of S325-1 to S325-2 as measured on the Pantone Scale.

Since the carbon black is incorporated into the polypropylene, it is captured in the final web. Therefore, the resulting web will not fade, is colorfast, and the carbon black pigment will not rub off.

Any method known to those in the art can be used to process the fibers or filaments into the web material. Two preferred methods are carding and spunbonding. The use of pigments in the fibers or filaments, however, can lead to difficulty in cleanup if used in the carding process, becoming costly and time consuming. A preferred method is spunbonding. In a preferred embodiment, polypropylene containing carbon black is spunbond to form the web. The weight of the web is from about 25 to about 40 gsm, more preferably from about 25 and about 35 gsm. Web material that has a higher weight may be stiff while web material with a lower weight may be thinner and more transparent.

In a process for making a spunbonded web, known amounts of polypropylene and pigment are mixed and then added to an extruder. The extruder's spinnerets lay separate fiber filament mixtures (web) onto a forming belt. The web is held onto the belt by vacuum. The web is then moved into a calendering apparatus, which embosses and bonds the web material. The surface of the embossed areas of the web is shiny and reflect light more than the dull, un-embossed areas of the web. Therefore, the amount of embossing determines the amount of light reflected.

In a preferred embodiment, the material is embossed with a repetitive pattern of shapes within a given area. For example, a series or a number of features, e.g, circles, triangles, squares, lines, honeycomb, diamond, etc. are embossed over the entire length and width of the outer surface of web. Each embossed feature has a major and minor axis extending therethrough, the major axis length being greater or equal to the minor axis length. In a preferred embodiment, the embossing is square shaped having a minor axis length being less than or equal to about 1 mm, such that about 5 to about 25% of the surface area is embossed. More preferably, about 15% of the cover surface area is embossed, which appears glossy and visually pleasing. In another preferred embodiment, the minor axis length is 0.75 mm and the major axis length is 0.80 mm, having about 12% of the cover surface area being embossed.

Preferably, there are about 25 to 65 embossed features per square centimeter of web surface area, more preferable about 30 to about 50 embossed features per square centimeter of web surface area. In another embodiment of the present invention, embossing is a continuous line that forms features or shapes.

Transfer Layer

The absorbent article of the present invention includes a transfer layer. The transfer layer may be made of any known material that will take up fluid and then distribute and release it to an adjacent absorbent core or layer for storage. Preferred transfer layers have a relatively open structure that allows for movement of fluid within the layer. Suitable materials for such transfer layers include fibrous webs, resilient foams, and the like.

The transfer layer is able to accept fluid and allow passage of the fluid through its mass to be absorbed by an adjacent absorbent core. Thus, transfer layers that are made of hydrophobic, nonabsorbent fibers may be able to accept large volumes of fluid into interfiber void spaces while the fibers themselves do not absorb any significant quantities of fluid. Likewise, open-celled foam structures that are made from nonabsorbent materials may also absorb fluid into the cells of the foam. The walls of the cells, however, do not absorb any fluid. The cumulative spaces within the transfer layer, i.e., the interfiber void spaces in the fibrous transfer layer or the open cells in the foam transfer layer, function much like a container to hold fluid.

Transfer layers that are made from webs of mostly absorbent fibers absorb the fluid as it enters the structure and do not distribute it throughout the rest of the structure as efficiently as webs containing non-absorbent materials. Preferred transfer layer fibrous webs include nonabsorbent materials to provide void volume and to allow for free movement of fluid through the structure. Examples of preferred materials include polypropylene, polyethylene, polyester, bicomponent materials, nylon and mixtures or combinations thereof. In a preferred embodiment, the transfer layer is an apertured film made from a carbon black pigmented polyethylene. An example useful in the present invention is a black topsheet film available from the ADMA division of Tredegar (Chieti, Italy) as 33-12-2001.

The transfer layer does not have to be apertured film; it can be any other pigmented nonwoven material, such as foam or netting, which transports fluid and in combination with the cover, provides masking of the absorbent core. However, in a preferred embodiment, the transfer layer is a 25 gsm apertured film made from pigmented polyethylene.

In a preferred embodiment, the absorbent core is masked by the combination of pigmented cover and pigmented transfer layer. In one embodiment, if the amount of pigment in the cover is slight or the weight of the cover material is low, the amount of pigment in the transfer layer may be such that the absorbent core is hidden from the naked eye.

The cover layer can be joined or laminated to the transfer layer by any methods known in the art such as fusion bonding, adhesive attachment, or by any other securement means. Fusion bonding includes heat bonding, ultrasonic bonding, and the like.

In a preferred embodiment, the cover and transfer layers are joined together by first applying adhesive to the underside of the cover material and placing the cover web onto the transfer layer material. While any adhesive may be used, such as any non-pressure sensitive adhesive, a preferred adhesive is D 1280 BE (available from Fuller Co., Germany)

The composite layer formed from the cover and transfer layers may be further processed. In a preferred embodiment, the composite layer includes an embossed pattern on the outer cover surface. For example, flowers and rails under the CAREFREE® pattern (e.g., U.S. Design Pat. No. 439,057) are embossed after the composite is formed, which results in an embossed pattern having flowers, rails, and squares.

Absorbent Core

The absorbent core or layer of the present invention may contain any known absorbent materials including, but not limited to, absorbent fibers, such as cellulose fibers, including, but not limited to wood pulp, regenerated cellulose fibers, and cotton fibers, rayon fibers and the like; superabsorbent fibers or particles; other naturally occurring absorbent materials, such as peat moss; and other synthetic absorbent materials, such as foams and the like. The absorbent layer may also include one or more of the following: thermoplastic binder fibers, latex binder, perfumes, oils or odor-controlling compounds. Additionally, the absorbent layer may be a mixture of two or more types of thermoplastic fibers having different melting points. Bicomponent fibers, fibers with an inner core of a thermoplastic fiber, e.g., polyester, surrounded by an outer sheath of thermoplastic, e.g., polyethylene, having a melting point much lower than the core, have been found to be the best fibers to work with from processing and performance standpoints. Upon application of heat and pressure sufficient to melt at least one of the fiber types, the remaining unmelted fibers will be thermobonded or fused together into a porous web.

Cellulosic pulp fibers can also be included with thermoplastic fibers. Since thermoplastic fibers, without further treatment, are essentially hydrophobic, the absorbent layer will not effectively draw fluid away from the composite cover and transfer layer absent some hydrophilic material. It is important to have sufficient pulp to absorb fluid.

In a preferred embodiment, the absorbent layer is made from airlaid pulp and includes about 15% by weight of superabsorbent polymer available as Salsorb CL 15 from Chemdal (United Kingdom). Optimally, the amount of superabsorbent in the absorbent core may be in the range of from about 5 to about 50% by weight of the absorbent core. The absorbent core may be compressed or uncompressed, embossed, or calendered. Additionally, the absorbent core may have the following dimensions: about 135 mm×about 38 mm×about 1.7 mm.

Backsheet

The backsheet of the present invention is a body fluid impervious black material, typically referred to as a "barrier," which is at least substantially impermeable to liquids. Its exterior forms the garment-facing surface of the absorbent article. The backsheet may be any thin, flexible, body fluid impermeable material, such as, but not limited to, a polymeric film, e.g., polyethylene, polypropylene, or cellophane, or a normally fluid pervious material that has been treated to be impervious, such as impregnated fluid repellent paper or non-woven material, including nonwoven fabric material, or a flexible foam, such as polyurethane or cross-linked polyethylene. In the present invention, the backsheet is a mixture of material and pigment. In a preferred embodiment, polyethylene is mixed with a known amount of carbon black to produce a black film. The thickness of the pigmented backsheet is from about 0.0005 to about 0.002 inch (about 0.013 mm to about 0.051 mm). In a preferred embodiment, the absorbent core is not visible to the naked eye when looking at the garment-facing surface of the absorbent article.

Optionally, the backsheet may be breathable, i.e., permits vapor to transpire. Known materials for this purpose include nonwoven materials, monolithic and microporous films in which microporosity is created by, inter alia, stretching an oriented film. Single or multiple layers of permeable films, fabrics, melt-blown materials, and combinations thereof that provide a tortuous path, and/or whose surface characteristics provide a liquid surface repellent to the penetration of liquids may also be used to provide a breathable backsheet.

Bonding Methods

The layers of the absorbent article may be, but not necessarily, bonded, e glued or adhered, to the adjacent layer. For example, the underside of the cover/transfer layer composite is adhered to the top side of the absorbent layer. The underside of the absorbent layer is adhered to the top side of the backsheet. As previously stated, any methods known in the art, such as fusion bonding, adhesive attachment, or by any other securement means can be used to secure the individual layers together to form the final absorbent article. Fusion bonding includes heat bonding, ultrasonic bonding, and the like.

Additionally, adhesive applied to the garment facing side of the absorbent article may be any adhesive known in the art. As a non-limiting example, pressure sensitive adhesive strips, swirls, or waves may be applied to help maintain the absorbent article in place. As used herein, the term pressure-sensitive adhesive refers to any releasable adhesive, or releasable tenacious means. Suitable adhesive compositions, include, for example, water-based pressure-sensitive adhesives such as acrylate adhesives. Alternatively, the adhesive composition may include rapid setting thermoplastic "hot melt," rubber adhesives, two-sided adhesive tape, and the like.

As is customary in the art, a paper release strip, which has been coated on one side, is applied to protect adhesive that may be applied to the garment-facing side of the backsheet. The coating on the paper release strip, which may be silicone, reduces the adherency to the adhesive of the coated side of the release strip. The release strip can be formed from any suitable sheet-like material which, when coated, adheres with sufficient tenacity to the adhesive to remain in place prior to use but which can be readily removed when the absorbent article is to be used.

Wings

Wings, also called, among other things, flaps or tabs, may also be part of the absorbent article of the present invention. Wings and their use in sanitary protection articles is described in U.S. Pat. No. 4,687,478 to Van Tilburg; U.S. Pat. No. 4,589,876 also to Van Tilburg, U.S. Pat. No. 4,900,320 to McCoy, and U.S. Pat. No. 4,608,047 to Mattingly. The disclosures of these patents are incorporated herein by reference in their entirety. As disclosed in the above documents, wings are generally speaking flexible and configured to be folded over the edges of the underwear so that the wings are disposed between the edges of the underwear.

The overall dimensions of the absorbent article of the present invention are preferably as follows: length is preferably in the range of about 3 inches (7.63 cm) to about 9 inches (22.9 cm). The maximum width of the anterior portion is preferably in the range of about 1.5 inches (3.81 cm) to 3 inches (7.6 cm).

The absorbent article of the present invention may be used with conventional underwear or may be shaped to conform to thong garments. As used herein, the term thong garment includes, but is not limited to, thong underwear, thong swimming suit bottom, G-strings, Rio cut underwear, Rio-cut swimming suit bottom, Brazilian cut underwear, Brazilian cut swimming suit bottom, and any other garment that exposes the buttocks, having a narrow strip of fabric or a cord that passes between the thighs supported by a waistband, a waist cord, belt or the garment itself.

The absorbent article may be applied to the crotch of a garment by placing the garment-facing surface against the inside surface of the crotch of the garment. Pressure sensitive adhesive may be applied to the garment-facing surface of the absorbent article to help secure it in place. As used herein, the term "pressure-sensitive adhesive" refers to any releasable adhesive or releasable tenacious means. Suitable pressure sensitive adhesives include for example water-based adhesives such as acrylate adhesives. Alternatively, the adhesive may comprise "hot melt" rubber adhesives or two-sided adhesive tape. Preferably, the pressure-sensitive adhesive is adhesive number D-39964-B available from Fuller Co. (Germany).

While the preferred embodiment of the invention is a black pantiliner, other embodiments are also included within the scope of the present invention. For example, other inert pigments may be used to produce a colored absorbent article. An example may be light or dark pigment, such as blue, green, pink, red, etc. Additionally, patterns including multiple colors and stripes, such as tiger, zebra stripes may be included.

EXAMPLE 1

Visual Masking Detection

Prototype devices made according to the present invention and a commercial absorbent product, available as ALLDAYS brand black pantiliner from Procter & Gamble (Cincinnati, Ohio), were compared for masking ability. In the central zone of the ALLDAYS brand black pantiliner, the white absorbent core is discernible, e.g., visible, to the naked eye when the perpendicular distance between the viewer's eye and the surface of the product is about 12 inches (about 30.5 cm) and the surface is illuminated with normal light, e.g., sunlight, or artificial light, e.g., fluorescent and incandescent, as described in U.S. Pat. No. 4,463,045. With the prototype device of the present invention, the white absorbent core was not visible to the naked eye when viewed in the same manner. Masking was further demonstrated by adding 1 ml of a synthetic menstrual fluid to a prototype device of the present invention and to the ALLDAYS product, then examining each product after various time points. The synthetic menstrual fluid used may be any synthetic menstrual fluid having a viscosity of approximately 30 centipoise. The red color of the synthetic menstrual fluid was not visibly detectable by viewing the surface of the prototype device with the naked eye. However, the red color of the synthetic menstrual fluid was clearly visible to the naked eye in the central zone of the ALLDAYS brand black pantiliner Viewing the prototype and ALLDAYS products at a moderate magnification also illustrated the superior masking of the absorbent article of the present invention. These results were shown using photographic techniques. Photomicrographs were prepared of magnified images of unstained and stained prototype and ALLDAYS products. Samples were imaged using an Olympus SZH stereo microscope with a 1xobjective, a zoom setting of 0.7 and a 2.5xeyepiece. A Javelin Chromachip $V^{tm}$ Hi Resolution color camera was used with the images printed on a Sony Mavigraph UP1900 MD video printer. Resulting images are at an original print magnification of 7.4x.

Figure 1:
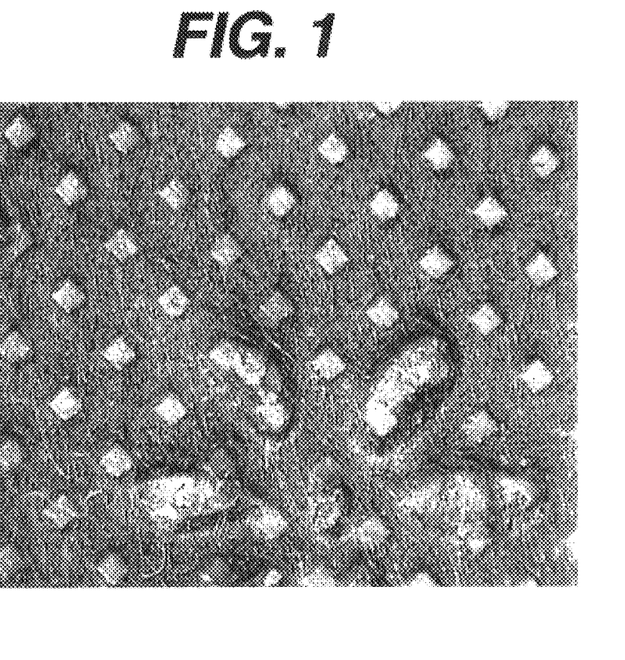
FIG. 1 is a color photograph of an unstained prototype made according to the present invention.
Figure 2:
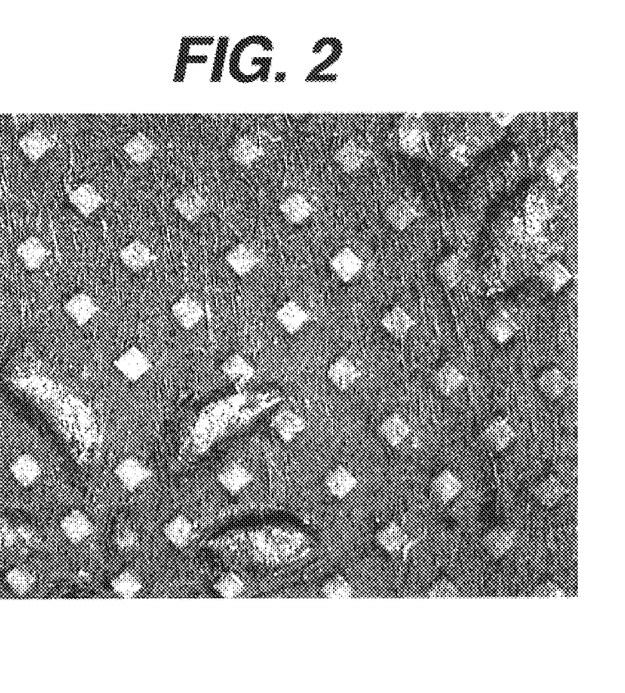
FIG. 2 is a color photograph of the prototype of FIG. 1 taken 15 minutes after synthetic menstrual fluid has been disposed on the cover.
Figure 3:
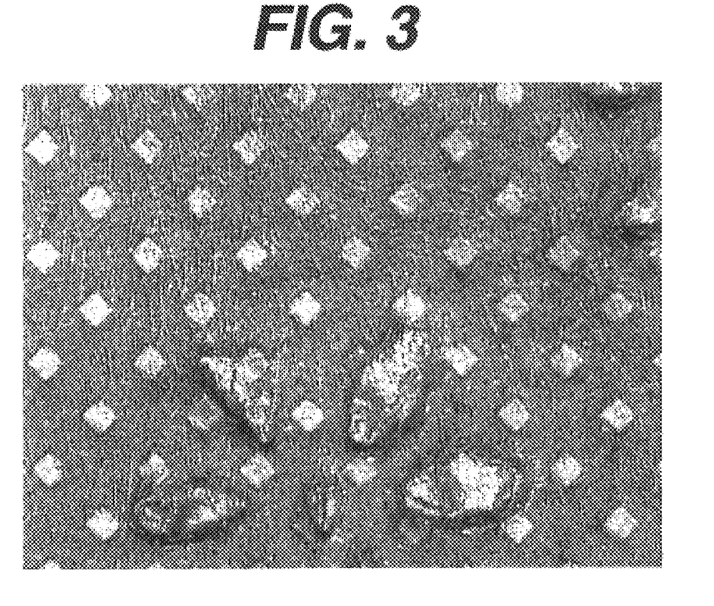
FIG. 3 is a color photograph of a prototype of the present invention taken 24 hours after synthetic menstrual fluid has been disposed on the cover.

FIG. 1 is a color photograph of an unstained prototype made according to the present invention. FIG. 2 is a color photograph of the prototype of FIG. 1 taken 15 minutes after synthetic menstrual fluid has been disposed on the cover. FIG. 3 is a color photograph of a prototype of the present invention taken 24 hours after synthetic menstrual fluid has been disposed on the cover.

Figure 4:
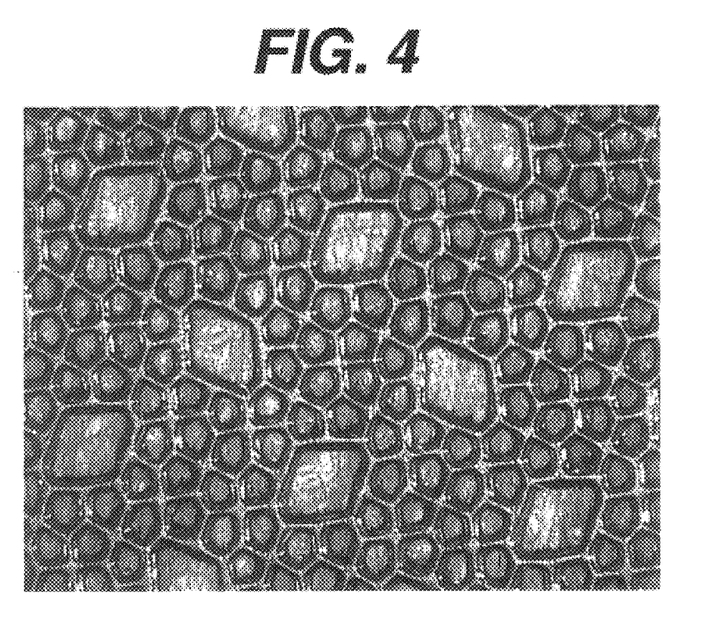
FIG. 4 is a color photograph of an unstained ALLDAYS black pantiliner.

FIG. 4 is a color photograph of an unstained ALLDAYS black pantiliner.

Figure 5:
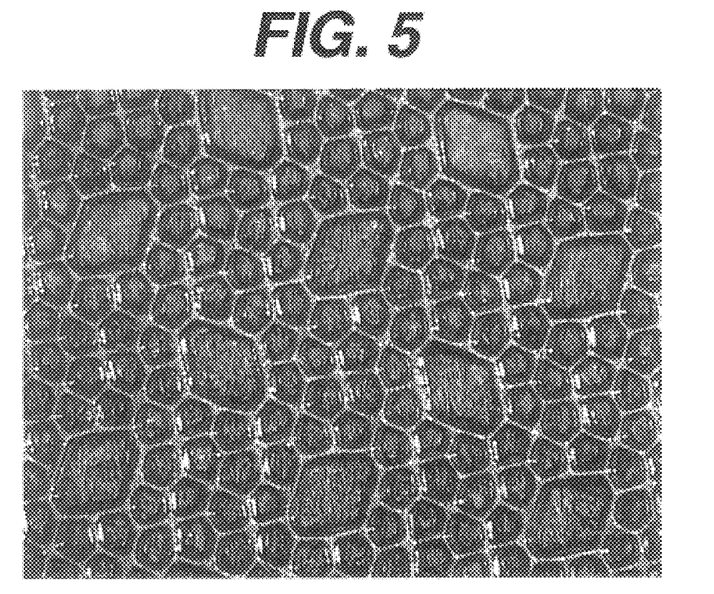
FIG. 5 is a color photograph of the ALLDAYS black pantiliner of FIG. 3 taken 15 minutes after synthetic menstrual fluid has been disposed on the cover.
Figure 6:
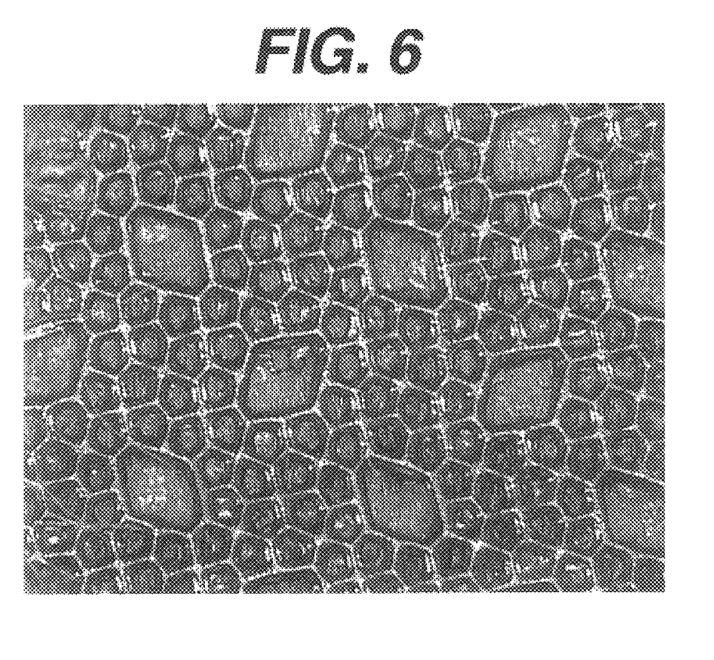
FIG. 6 is a color photograph of an ALLDAYS black pantiliner taken 24 hours after synthetic menstrual fluid has been disposed on the cover.

FIG. 5 is a color photograph of the ALLDAYS black pantiliner of FIG. 3 taken 15 minutes after synthetic menstrual fluid has been disposed on the cover. FIG. 6 is a color photograph of an ALLDAYS black pantiliner taken 24 hours after synthetic menstrual fluid has been disposed on the cover.

Figure 7:
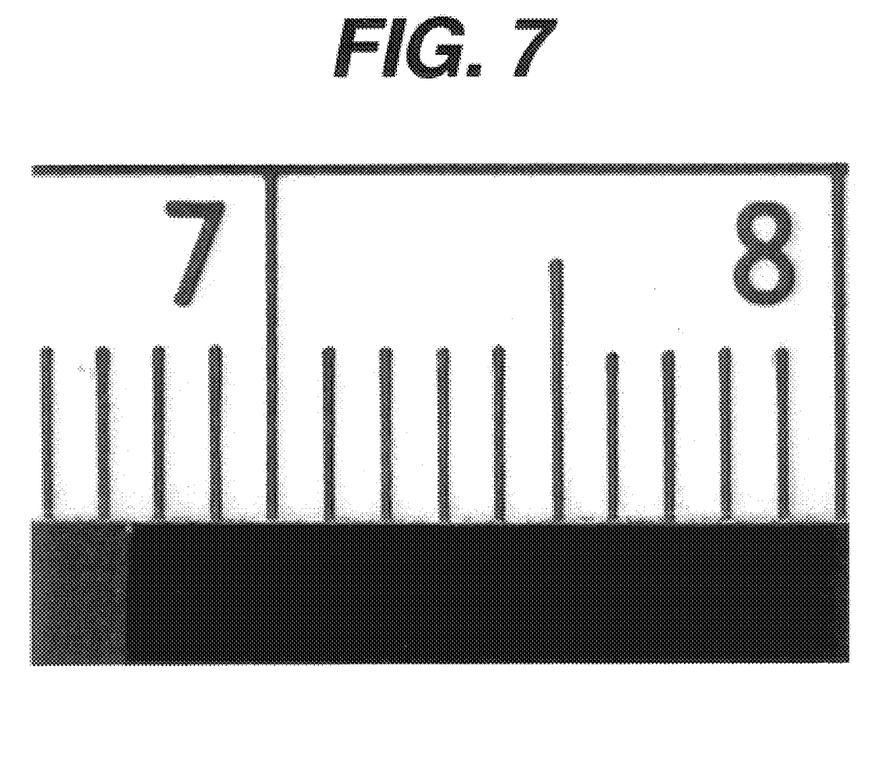
FIG. 7 is a color photograph of the scale used in the color photographs set forth in FIGS. 1–6.

FIG. 7 is a color photograph of the scale used in the color photographs set forth in FIGS. 1–6.

As is depicted in FIGS. 5 and 6, the ALLDAYS black pantyliner failed to mask the red color of the synthetic menstrual fluid at 15 minutes and 24 hours after the synthetic menstrual fluid was deposited thereon. This result was consistent with inspection by the naked eye. In contrast, the prototype absorbent article of the present invention did not permit any red color of the synthetic menstrual fluid to be detected by either the naked eye or microscopic examination, as demonstrated in FIGS. 2 and 3.

The specification and examples above are presented to aid in the complete and non-limiting understanding of the invention disclosed herein. Since many variations and embodiments of the invention can be made without departing from its spirit and scope, the invention resides in the claims hereinafter appended.

We claim:

1. A discrete absorbent article comprising:
   a) a single carbon black pigmented polypropylene cover layer having a surface area, wherein the cover layer comprises a pattern of embossed features, each embossed feature comprises a major axis length and a minor axis length, wherein the major axis length is greater than or equal to the minor axis length;
   b) a carbon black pigmented polyethylene apertured transfer layer;
   c) an absorbent core; and
   d) a carbon black pigmented polyethylene backsheet.

2. An absorbent article of claim 1, wherein the minor axis length is equal to or less than about 1 mm.

3. An absorbent article of claim 1, wherein the embossed feature comprises about 5 to 25%,of the surface area of the cover layer.

4. An absorbent article of claim 3, wherein the embossed feature further comprises 15% of the surface area of the cover layer.

5. An absorbent article of claim 1, wherein the embossed feature is selected from the group consisting of squares, circles, diamonds, triangles, and lines.

6. An absorbent article of claim 5, wherein the embossed feature comprises squares.

* * * * *

UNITED STATES PATENT AND TRADEMARK OFFICE
CERTIFICATE OF CORRECTION

PATENT NO.    : 6,586,653 B2
DATED         : July 1, 2003
INVENTOR(S)   : Graeme, III et al.

It is certified that error appears in the above-identified patent and that said Letters Patent is hereby corrected as shown below:

Column 2,
Line 16, "93/097744" should read -- 93/09744 --

Signed and Sealed this

Sixteenth Day of March, 2004

JON W. DUDAS
*Acting Director of the United States Patent and Trademark Office*